United States Patent [19]
Stover et al.

[11] Patent Number: 6,091,493
[45] Date of Patent: Jul. 18, 2000

[54] PROCESS FOR PARTICLE SIZE MEASUREMENT

[75] Inventors: John C. Stover; Craig A. Scheer, both of Charlotte, N.C.

[73] Assignee: Scatter Works, Inc., Charlotte, N.C.

[21] Appl. No.: 09/281,611

[22] Filed: Mar. 30, 1999

Related U.S. Application Data

[60] Provisional application No. 60/079,901, Mar. 30, 1998.

[51] Int. Cl.[7] .................................................. G01N 21/00
[52] U.S. Cl. .......................... 356/336; 356/237.4; 702/29
[58] Field of Search ............................. 356/237.1, 237.2, 356/237.3, 237.4, 237.5, 335, 336, 339, 338, 239.7, 239.8; 364/552, 555, 468.17, 150; 377/11; 348/126; 382/149, 147, 225; 702/35, 29

[56] References Cited

U.S. PATENT DOCUMENTS

| | | | |
|---|---|---|---|
| 4,242,673 | 12/1980 | Cooper | 356/439 |
| 5,801,824 | 9/1998 | Henley | 356/339 |
| 5,801,965 | 9/1998 | Takagi et al. | 702/35 |
| 5,909,276 | 6/1999 | Kinney et al. | 356/336 |
| 5,936,726 | 8/1999 | Takeda et al. | 356/237.2 |

*Primary Examiner*—Hoa Q. Pham
*Attorney, Agent, or Firm*—Madson & Metcalf

[57] ABSTRACT

The method of the present invention accurately measures the diameter of a particle resting on a surface through use of a beam of known wavelength being directed at the surface at an incident angle. Scattered light measurements are taken as the beam contacts the surface and the particle. Scattered light measurements are separated into their respective P and S power components. During all measurements, the beam source remains constant in that it is not moved or adjusted for intensity or polarization. The P and S power components of the background measurements are subtracted from the P and S power components of the particle measurements to give net P and S power components. From the net P and S power components the net P and S components of the differential scatter cross section may be derived as is known in the art. Different ratios may be formed from the differential scatter cross section to eliminate many of the intensity errors inherent in the use of scattered light measurements. These ratios are sensitive to particle diameter but insensitive to absolute light measurements.

A model, known in the art for its accuracy, is used to calculate scattered light of the particle. The model results are used to form the same ratios as a function of particle diameter and are then compared to the ratios from the measured data. Based on this comparison, the diameter of the spherical particle is determined.

34 Claims, 5 Drawing Sheets

Comparison of 2 Particle Sizes with 2 Polarizations

Comparison of Ratioed Rps/Rps and 2* Rps width

PROCESS FOR PARTICLE SIZE MEASUREMENT

RELATED APPLICATION

This application claims priority to U.S. provisional patent application Ser. No. 60/079,901, filed Mar. 30, 1998.

BACKGROUND OF THE INVENTION

1. The Field of the Invention

The invention relates to a process for accurately measuring particles which are deposited on a surface. More specifically, the invention relates to a process for accurately measuring the diameter of particles which are used to calibrate industrial particle scanning tools.

2. Technical Background

Particle scanners are used in the chip manufacturing industry to detect contamination on extremely smooth surfaces such as silicon wafer surfaces. Superior quality and performance in the silicon wafer surfaces is achieved if the surfaces are free of imperfections and contaminations. Particle scanners operate by sensing scattered light from imperfections and contaminations on the surface as a laser is scanned over the surface.

The particle scanners are calibrated before scanning wafer surfaces to ensure their sensitivity and accuracy. Calibration of the particle scanners involves the particle scanners measuring the light scatter off of particles of predesignated size. In this manner, the accuracy of the particle scanners readings is compared with the known particle size.

One common type of particle deposited on the wafer surface are spherical polystyrene latex spheres (PSL's). In most cases the diameter of these spheres is known only to about 10%. However, it has been shown by National Institute of Science and Technology (NIST), that sphere diameters vary by as much as 25% depending on sphere size and sphere manufacturer. Because the scatter varies significantly with sphere diameter, knowing the true diameter of a PSL is an important scanner calibration issue. Greater calibration accuracy is achieved by more accurately knowing the PSL diameter.

PSL diameters are extremely small and may range from micrometers to nanometers. Often times improving the measurement of PSL's to less than 10% error is not economically feasible using conventional methods.

Various technologies exist for measuring PSL diameters and include using scattered light to take measurements. Many of these methods make use of particles suspended in a fluid (either gas or liquid).

A technique currently employed in the semiconductor industry is to measure the size of the particles in an electrostatic classifier. Charged particles, moving in a flow of air, are turned towards a small opening through the influence of an electric field generated by an applied voltage. Resistance to turning comes almost entirely from air resistance, which depends on particle diameter. Thus the amount of bending is determined by a combination of particle diameter, flow rate and applied electric field. Only particles of a particular size (regardless of material composition) get through the opening at a fixed voltage. The determination of particle diameter is made from a first principles calculation of this process and relies on having very accurate values of system geometry, applied voltage and flow rate. Accurate measurements from this method often have a 10% or more error rate.

Industry practice has had to accept inaccurately measured PSL's for calibration testing. An important issue for developing particle scanners is optimizing sensitivity for a production environment. Improved calibration methods would greatly enhance particle scanner sensitivity.

Thus, it would be an advancement in the art to produce a process to accurately, reliably, and economically measure PSL sphere diameter.

Such a method is disclosed and claimed herein.

BRIEF SUMMARY OF THE INVENTION

The method of the present invention accurately measures the diameter of spherical and small non-spherical particles. A beam of a known wavelength is directed at a surface at an incident angle. The beam is polarized with a known power distribution of the beam into P and S components. Some approaches use 100% P light, some use 100% S light, and some use a mix of S and P components. Scattered light measurements are taken as the beam contacts a section of the surface completely free of particles to measure the background scattered light of the surface. The background measurements are separated into their respective P and S power components.

Scattered light measurements are next taken off a particle resting on the surface to measure the scattered light of the particle and background. As before, the particle measurements are separated into their respective P and S power components. During all measurements, the beam source remains constant in that it is not moved or adjusted for intensity or polarization. The P and S power components of the background measurements are subtracted from the P and S power components of the particle measurements to give net P and S power components. From the net P and S power components the net P and S components of the differential scatter cross section may be derived as is known in the art.

Ratios are then formed to define parameters that are independent of measurement intensity errors. One method is to simply ratio net scatter values taken at two different scatter angles, but taken at the same polarization to obtain a sizing parameter. Another method is to derive a ratio function, Rps, from the net P and S components of the differential scatter cross section. The function Rps can then be used to derive one or more different sizing parameters. These ratios and the resulting parameters are sensitive to particle diameter but insensitive to absolute light measurements.

A model, known in the art for its accuracy, is used to calculate scattered light of the spherical particle. One such model is known in the art as the DDSURF model which has been developed at Arizona State University. Another model is the POLAR Model developed at Moscow State University. The model does not calculate any background scatter. The model results are used to find the same parameters as a function of particle diameter. Based on this comparison, the diameter of the particle is determined.

BRIEF DESCRIPTION OF THE DRAWINGS

In order that the manner in which the above-recited and other advantages and features of the invention are obtained, a more particular description of the invention summarized above will be rendered by reference to the appended drawings. Understanding that these drawings only provide a selected embodiment of the invention and are not therefore to be considered limiting of its scope, the invention will be described and explained with additional specificity and detail through the use of the accompanying drawings in which.

DESCRIPTION OF THE PREFERRED EMBODIMENTS

Figure 1:
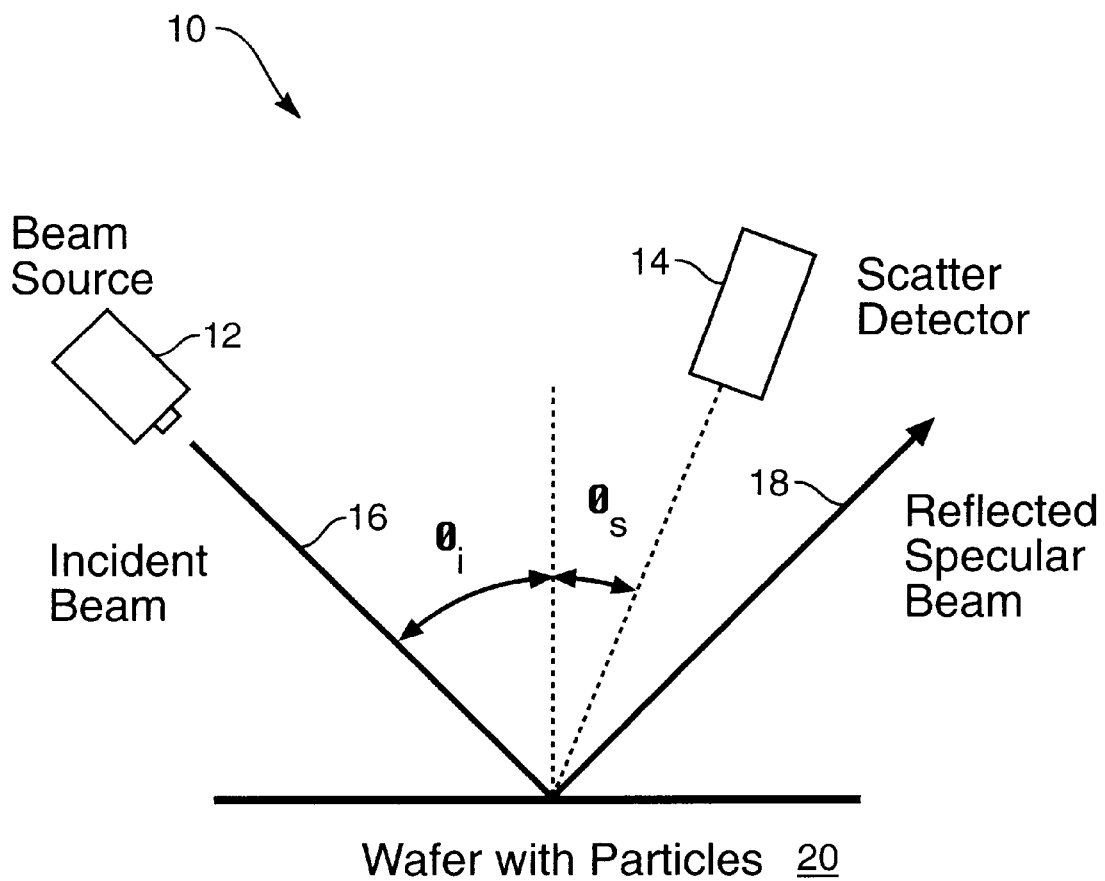
FIG. 1 is a block diagram of one apparatus suitable for use with the process of the present invention.

Reference is now made to the FIGS. 1 through 5 wherein like parts are referred to by like numerals throughout.

Mathematical models have been developed at several facilities to predict how light scatters from small particles on flat reflective surfaces. Some of these models have been reduced to user friendly software codes that allow the scattered intensities to be studied as a function incident angle, wavelength, and polarization characteristics. In the semiconductor industry, these models have been used to optimize the design of particle scanners that use scattered laser light to detect and map contamination on wafer surfaces.

The present invention is a process resulting from model research to accurately determine particle size in a lab environment where accuracy, not speed, is the issue. The process requires experimental data, obtained from published measurement techniques, and the use of a model for analysis. The process defines the geometry of the measurements and the analysis required to reduce the uncertainty associated with determination of particle diameter that is caused during the measurement process. Several analysis techniques are discussed and disclosed herein.

Two conventional technologies are required to perform the method of the present invention. The first of these is an accurate model of particle scatter. At least two such mathematical approaches have been used to accurately model scatter from spherical surface bound particles. One is the discrete dipole (or DD) approach, which has been reduced to the successful model, DDSURF, at Arizona State University. A second mathematical approach is the discrete sources method (or DSM). DSM has been used in the POLAR Model developed at Moscow State University. When DDSURF and POLAR are compared to each other for the case of low index particles, such as PSL's, with diameters smaller than a light wavelength, they give almost exactly the same results. The POLAR Model has been experimentally confirmed to about 5% level of error, and most of this error is in the measurement. This means that both the DD and DSM mathematical approaches to modeling are valid. Further information regarding an acceptable model may be found in the publication, Yu. Eremin, and A. Sveshnikov "The Discrete Sources Method for Investigating Three Dimensional Electromagnetic Scattering Problems," Electromagnetics, vol. 13, pp. 1–22, January 1993. The present invention uses a model based on the DSM mathematics.

Both of these models calculate scatter from particles on a perfectly smooth surface. Effects from surface roughness, and other sources of non-particle scatter, are not included in the models. Both models present scatter data in units of differential scattering cross-section (DSC), which is simply the scattered light per unit solid angle (as watts per steradian) divided by the incident intensity at the particle (as watts per unit area). DSC has units of area per steradian.

The second technology needed to apply the particle measuring process of the present invention is that of accurately measuring particle scatter. Conventional methods are published and well known in the art and employ a lab scatterometer to take measurements in either single particle or multiple particle situations. The methods require that other, non-particle, sources of scatter are first measured. The non-particle scatter sources result from surface roughness and air molecules. The resulting measurement is then subtracted from the measurement made of the particle. These measurements are the same ones used to confirm the POLAR model in the published literature.

A problem is that intensity errors in the measurements can introduce some uncertainty into calculated particle diameter if sizing is attempted by simply comparing measured and modeled scatter patterns. The reason for the intensity errors depends on the technique employed. For single particle measurements, the measurements are made with a sharply focused beam, generally between 10 to 100 $\mu$m across. The center of the focused spot on the surface is brighter than the edges, with the intensity falling off in something like a Gaussian distribution. In order to calculate the DSC, the light intensity at the particle must be known, and this is difficult to accurately determine for very small spot sizes. If a large illumination spot is used to obtain the average scatter from hundreds of particles, then the particle density (in particles per unit area) must be known, and this is difficult to accurately determine or confirm.

The present invention allows these errors to be ratioed out prior to the final comparisons between measurement data and modeled data, resulting in a significantly more accurate determination of particle diameter.

The present invention can be used with measurement data from either the single particle or multiple particle measurements. As described below, it makes use of measurements in the incident plane, but it is clear that the process can be applied to out-of-plane scatter as well.

The method of the present invention begins with a prior knowledge of the approximate particle diameter (i.e.: the manufacturers published diameter). Based on the approximate particle diameter, the operator selects a light wavelength and incident angle for the measurement. This choice is made on the basis of experience with the process. Different configurations are more accurate for certain particle diameters. The approximate diameter needs to be known only to about 100% so the manufacturer's nominal diameter is more than sufficient for this step. If the manufacturer's nominal diameter is not known, then the entire process can be repeated.

Referring to FIG. 1, a commmercially available scatterometer suitable for use with the present invention is shown and generally designated 10. FIG. 1 illustrates the geometry of the scatterometer 10 used to take scatter data. The scatterometer 10 comprises a conventional laser beam source 12 and a conventional scatter detector 14. The operator sets the beam source 12 at the appropriate angle of incidence $\theta_i$ and wavelength. The beam source 12 produces a laser beam or incident beam 16. The laser beam 16 is directed to a surface 20, such as a wafer surface.

A reflected specular beam 18 and resulting scatter are produced from contact with the surface 20. The detector 14 swings from the negative scatter angles, $\theta_s<0$ on the left, through 0 at surface normal and finally through the positive scatter angles on the right. The measurements of the scatterometer are converted into the same scatter intensity units used in the present invention.

In operation, the operator sets the laser beam 16 at a known source polarization. There are several choices, but S, P and 45 degrees are useful. The 45 degree choice places 50% of the incident light in a P polarization and 50% in an S state. In this condition, there will be both S and P polarized light in the scattered field measured in the incident plane. With the sample removed, the operator measures the power in the S and P components of the beam 16. These powers are designated as Psi and Ppi. These values will be used in the calculation of DSC.

In one presently preferred embodiment, the operator takes two measurement scans of scattered intensity in the incident plane using only one polarization, either P or S. Once the measurements have started, the source 12 is never adjusted. The measurements are taken in two sets. The first set is with the particle or particles outside the illuminated spot, and is used to obtain the background scatter caused by surface roughness. The first set of measurements may be referenced as the background set.

The second set of measurements is identical to the first, but with the beam 16 approximately centered on the particle or in the multiple particle deposition. The particle or particles must be from a known material, such as polystyrene latex, and is the same material used in the model. The invention makes use of PSL's herein but one of skill in the art will appreciate that particles of other substances which have been modeled may be used and are within the scope of the invention.

The beam 16 is centered on the particle or particle deposition by moving the wafer surface 20 in the plane of the wafer surface 20. As previously stated, the beam source 12 is not moved or adjusted while taking measurements. Thus, there is no change in the intensity or polarization of the source beam. The background set of measurements is then subtracted from the second set of measurements and the net scatter is converted into particle DSC in the conventional manner. The resulting DSC may be an S polarization DSC (DSCs) if an S polarization was used or a P polarization (DSCp) if a P polarization was used.

In another preferred embodiment, the operator takes four scans so that both P and S polarization are used. Additional source polarizations are possible and, although they are not detailed, it would be clear to one skilled in the art that they are covered by the technique of the present invention. In this method, two background sets of measurements are taken, one for P scattered light and the other for S scattered light. The polarization filtering of the scattered light may be done at the detector 14.

Two more sets of measurements, one for P scattered light and one for S scattered light, are taken with the beam 16 approximately centered on the particle or in the multiple particle deposition. As with the previously described method, the beam 16 is centered on the particle or particle deposition by moving the wafer surface 20 in the plane of the wafer surface 20.

The P and S background sets of measurements are subtracted from their respective P and S second sets of measurements. The net scatter for P and S is converted into DSCp and DSCs respectively. These data scans will be used to define parameters that are very sensitive to changes in particle diameter, but insensitive to measurement uncertainty. One of skill in the art will appreciated that many parameters can be defined.

Figure 2:
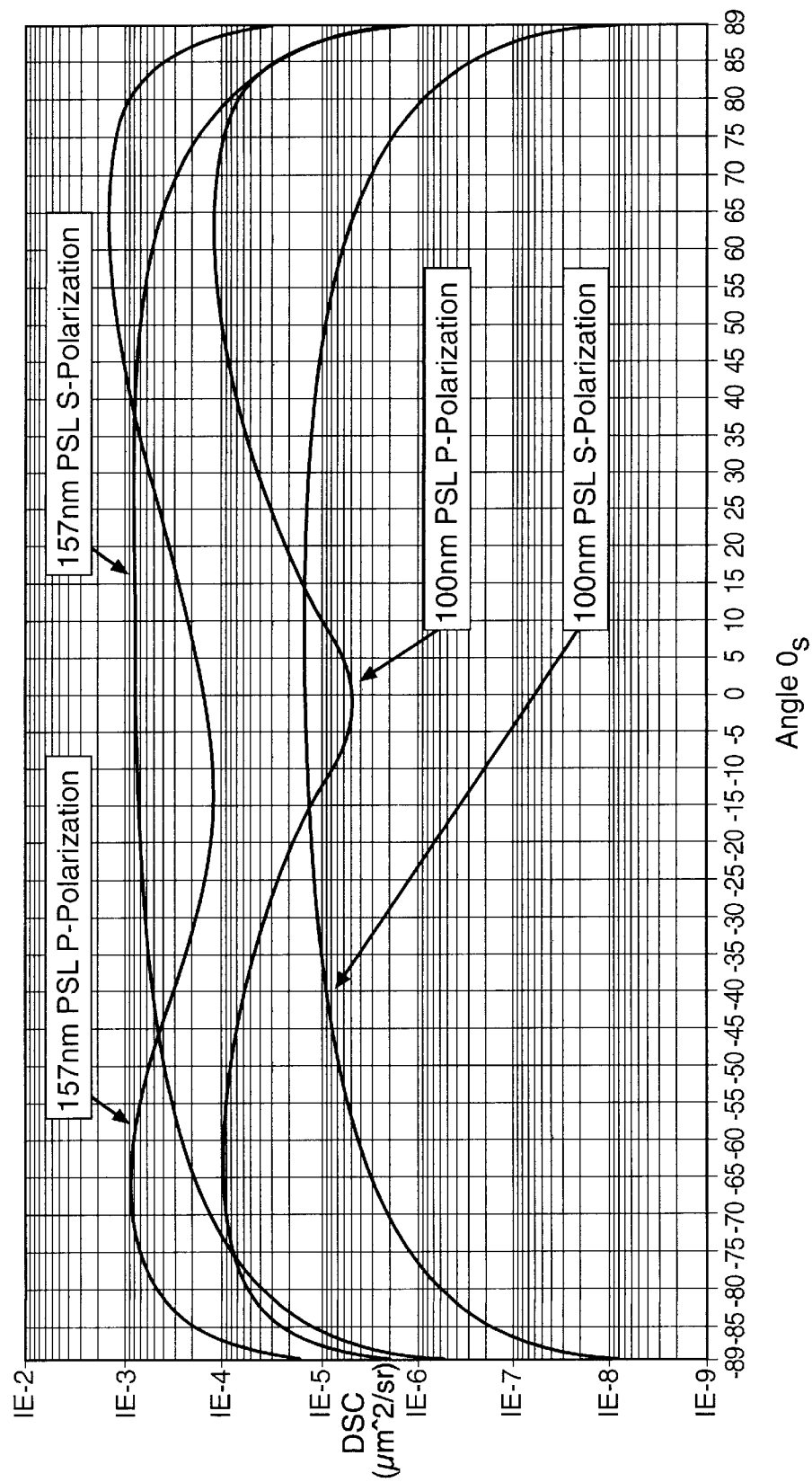
FIG. 2 is a graph comparison of scatter from 2 particle diameters with 2 polarizations.

Referring to FIG. 2, modeled DSC's for two diameters of PSL spheres at S and P polarizations are shown as a function of the scatter angle $\theta s$, the shape of the plotted curves changes with diameter. In particular, a dip associated with DSCp moves to the left with an increase in particle diameter. The magnitude of the DSC also increases, but this error prone variable is canceled out when a ratio, Rps, is formed. More to the point is that the ratio between DSCs and DSCp changes with particle diameter.

A preferred parameter is calculated from the DSCp data set by choosing two DSCp values on either side of the prominent dip in this curve and ratioing them to form the ratio, $R=DSC_{right}/DSC_{left}$. The dip in DSCp is clearly evident when either of the DSCp curves of FIG. 2 are examined. The value R is insensitive to the gain intensity errors found in most scatter measurements because these percentage errors cancel out when the ratio is taken. The value R is extremely sensitive to particle diameter. This can be seen by looking at the two DSCp curves in FIG. 2. The dip moves to the left as the particle diameter increases. Thus a small increase in particle diameter will decrease the value of $DSC_{left}$, but increase $DSC_{right}$, because these are evaluated at fixed angles. The result is that R decreases dramatically as particle diameter increases.

The same situation is then created in the scatter model. The parameter R is evaluated in the model for a large number of closely spaced particle diameters. This list of model parameters is then compared to the value of R obtained experimentally to determine the actual particle diameter. The method has been shown to be accurate to about 1% when compared to a few carefully calibrated particles sized at NIST using a different technique. Of course it is clear to one versed in the art that many different ratios could be used, involving two or more DSC values to create particle diameter sensitive parameters.

Similar situations can be generated by ratioing DSCs and DSCp to form Rps=(DSCp)/(DSCs). Rps is sensitive to particle size but is insensitive to absolute light measurements. By ratioing the two DSC's, the result is independent of the largest sources of error associated with DSC measurements. Because the source beam 16 was not moved between measurements, the percent errors associated with calculation of the incident intensities and/or particle density will be equal. By ratioing the DSC's, these percent errors cancel out. In addition, any uncertainty in the solid angle of the receiver is also canceled out. The result is that the data represented by Rps depends very strongly on particle properties and only very weakly on uncertainties in the measurement parameters. In particular, the data set Rps depends on the ratio of intensity shapes between the two polarizations with scattering angle, and not at all on the ability to measure absolute scattering intensities.

Figure 3:
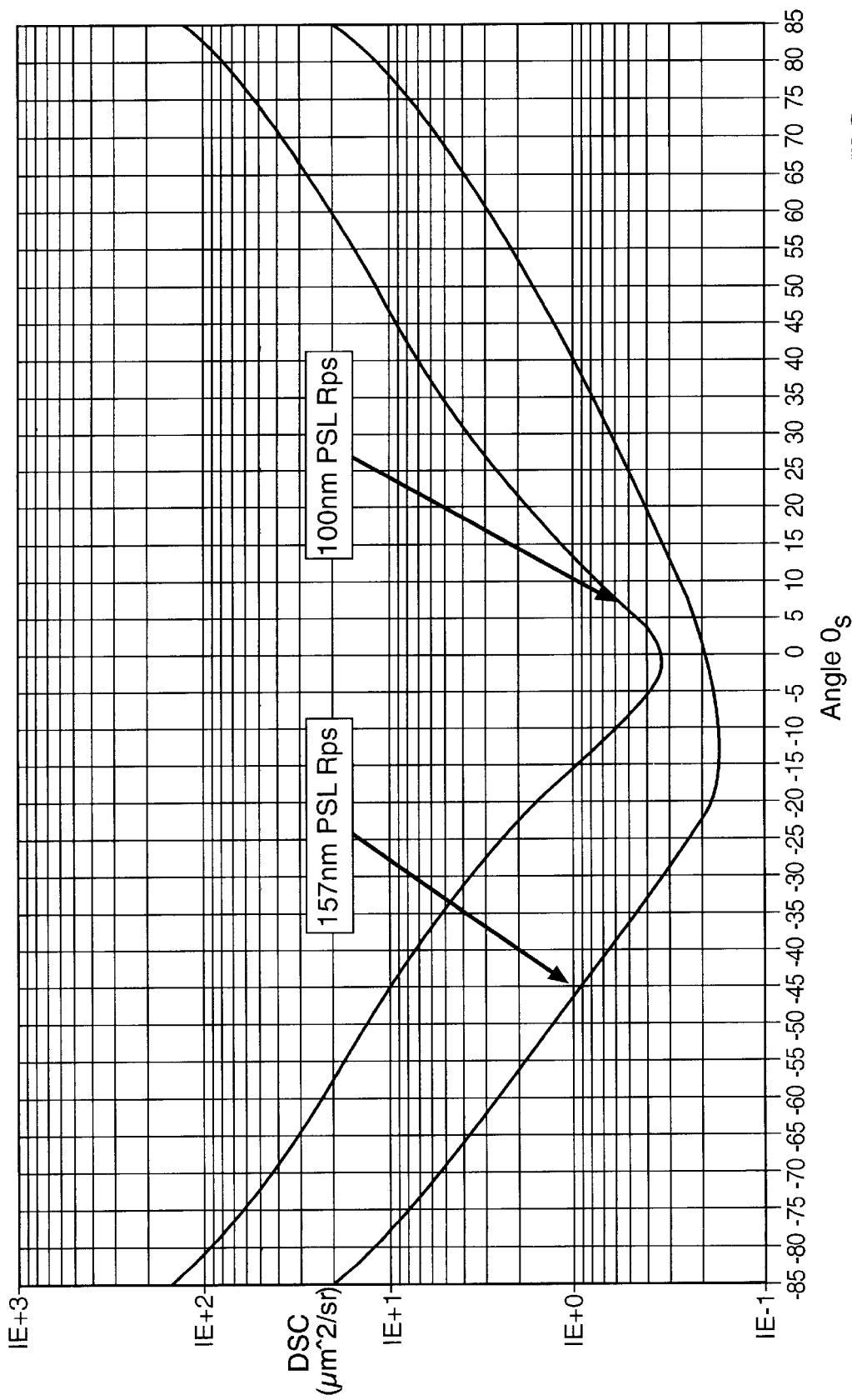
FIG. 3 is a graph comparison of the Rps ratio of 2 particle diameters.

Referring to FIG. 3 the two Rps's from the modeled results of FIG. 2 are shown. Several diameter sensitive parameters may be formed from Rps to find particle diameter. In one embodiment, the method is to simply compare the modeled and measured data sets of Rps. Particular diameters for modeled data sets are known. Thus, a modeled data may be chosen that best fits the measured data set to determine a particle diameter. Although this method works and is within the scope of the present invention, it is not a preferred method as it requires extra time and some qualitative judgment. Faster, more quantitative methods to extract particle diameter from Rps are preferred. Three such methods follow. Accuracy depends on the angle of incidence $\theta i$ and the particle diameter range.

One method to determine particle diameter from R or Rps simply involves measuring the location of the dip angle in either R, Rps or DSCp. The location of the dip angle along the x-axis may be referenced as θmeas. The location of the measured dip angle θmeas is then compared to the dip location for the model which may be referenced as θmod. Since dip location, dip depth, and dip width change with diameter, and all vary with incident angle, this comparison of the measured results to the model has to be done at exactly the same incident angle. Fortunately measurement and model angles can be obtained very accurately, on the order of 0.01 degrees.

The variation of $\theta_{mod}$ may be found from the model for any situation, but FIG. 2 can be used again to illustrate the situation. The dips for the 100 nm and 157 nm DSCp curves are about 12 degrees apart, or about 5 nm/degree. The uncertainty in the angle measurement is less than 0.1 degrees, so the sensitivity is about 0.5 nm. One difficulty with this approach is that it involves using the region of R or Rps where the signals were the lowest.

A second method to determine particle diameter from R or Rps involves comparing the minimum values of R or Rps for the measured and modeled results. The minimum values of R or Rps are found at the dip angle and are referenced herein as MINmod and MINmeas. Variation of MINmod with PSL diameter is also shown in FIG. 3. This method also suffers from using the low signal region of the data set.

The problem with using the very lowest signal region can be avoided if a parameter is formed on the basis of dip width. It is clear from FIG. 2 that dip width increases with particle diameter. Anyone versed in the art will recognize that many versions of this technique are possible, and only two are mentioned here. One way is to define dip width as the width where Rps is twice the value at the dip; however, this again means knowing the dip value.

Figure 4:
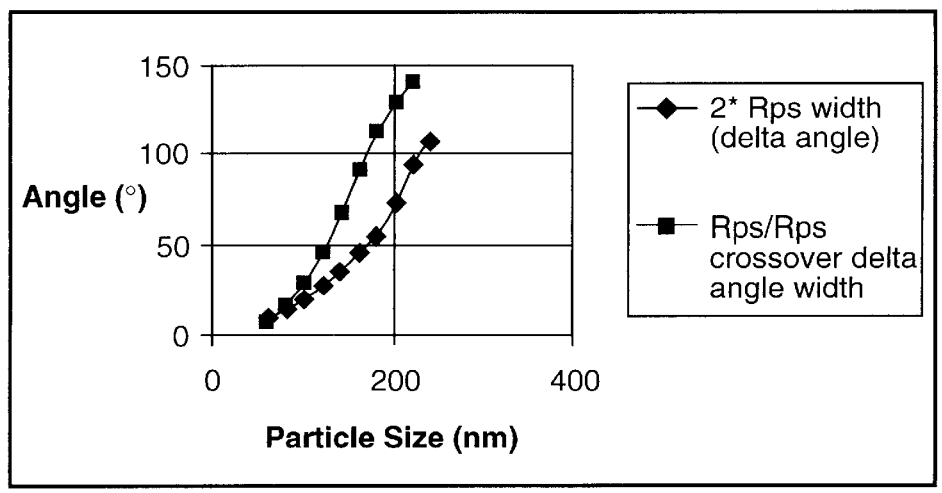
FIG. 4 is a graph comparison of Rps/Rps and 2 times Rps width.

Referring to FIG. 4 the relationship between particle size and the width defined at twice the dip value (2*Rps width) is shown. A better way to exploit dip width is to form Rps and 1/Rps on the same plot. In 1/Rps, the dip becomes a peak and the two curves cross each other on either side of θ, defining a width that changes quite rapidly with particle diameter. The location of these cross over points always comes when Rps equals 1/Rps equals 1.0, so this dip width is called $WID_1$. This location may be found without evaluating 1/Rps. FIG. 4 shows $WID_1$ plotted vs. particle diameter again using a 488 nm wavelength source at incident angle of 70 degrees. The slope is about 1 deg/nm and implies an uncertainty in the diameter measurement of less than 1 nm. The usable range for this chart is about 60 nm to 210 nm. Changing the incident angle will shift the useable range. A similar technique may be used for the parameter R.

In addition to the particle scatter signal, the experimental data contains a small variation due to a "laser speckle" signal that is caused by surface roughness. This small variation modulates the larger background signals that have been removed. Because this modulation is not exactly identical between the background measurement and the particle measurement, it can not be subtracted out. If the particle signal is small, then this speckle modulation has to be removed from the experimental data prior to comparison with the model. It consists of wiggles on the DSC that come every few degrees, depending on spot size. Because the illuminated spot is always significantly larger than the particle, this modulation noise will always vary at a higher frequency than the particle signal. As a result, it can be removed by either curve fitting or, equivalently, low pass filtering.

A number of particle sizes have been evaluated using the two scan approach where the parameter R is defined as DSCright/DSCleft. These measurements have been performed on particles that were sized at NIST by entirely different techniques. The table shown below gives the results of this work. The uncertainties are 95% levels (sometimes called two sigma) and are found by applying the model to known measurement uncertainty. It is clear that the method employed in the present invention works. Similar results were obtained when the Rps crossover width parameter was used.

| Invention Result | NIST Result |
| --- | --- |
| 76.4 +/− 0.9 nm | 76.17 nm (Approximate Evaluation) |
| 100.3 +/− 1.1 nm | 100.7 +/− 1.0 nm |
| 126.0 +/− 1.4 nm | 126.9 +/− 1.4 nm |
| 215.9 +/− 2.5 nm | 217.7 +/− 3.4 nm |

Figure 5:
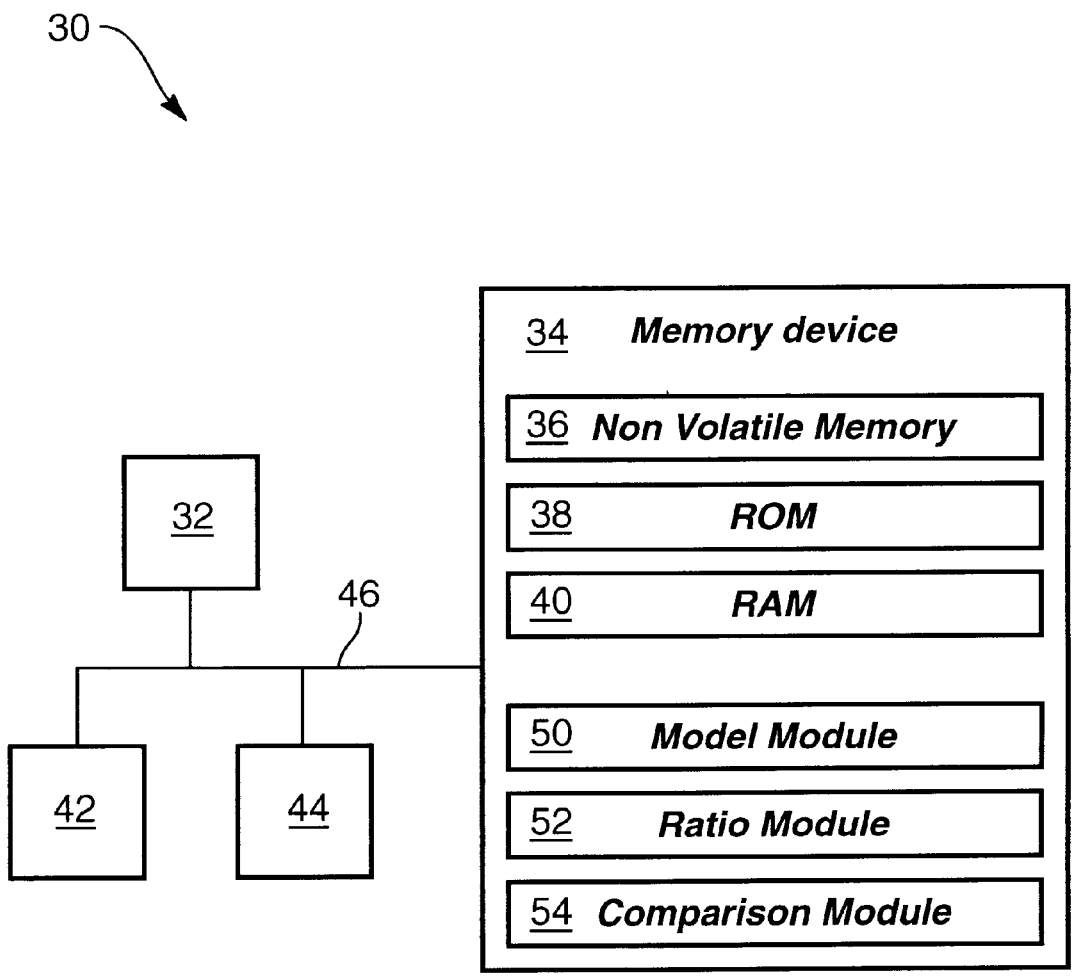
FIG. 5 is a schematic block diagram of one embodiment of an architecture of a system configured in accordance with the invention.

The methods of the present invention may be performed manually or by computer implemented assistance. Referring to FIG. 5, a computer system 30 capable of implementing some of the methods of the present invention is shown. The computer system 30 comprises a processor 32 or CPU 32 which is operably connected to a memory device 34. The processor 32 executes algorithms to determine the particle diameter based on the measurements of light scatter from the background and the particle or particles.

The memory device 34 may include one or more devices such as a hard drive or nonvolatile storage device 36, a read-only memory 38 (ROM), and a random access memory 40 (RAM).

The computer system 30 may include an input device 42 for receiving inputs from a user or another device. An input device 42 may include one or more physical embodiments. For example, a keyboard may be used for interaction with an operator, as may a mouse or a stylus pad. A touch screen, a telephone, or simply a telephone line, may be used for communication with other devices, users, or the like. Similarly, a scanner may be used to receive graphical inputs which may or may not be translated to other character formats. A memory device of any type (e.g. hard drive, floppy, etc.) may be used as an input device, whether resident within the system 30. The input device 42 allows measurement data relating to scattered light to be inputted to the system 30.

The system 30 may also comprise an output device 34. The output device 44, like the input device 42, may include one or more hardware units. A monitor may provide outputs to a user for feedback during a process, or for assisting two-way communication between the processor 32 and a user. A printer or a hard drive may be used for outputting information as the output device 44.

Internally, a bus 46 may operably connect the processor 32, memory devices 34, input device 42, and output device 44. The bus 46 may be thought of as a data carrier. As such, the bus 46 may be embodied in numerous configurations. Wire, fiber optic line, wireless electromagnetic communications by visible light, infrared, and radio frequencies may likewise be implemented as appropriate for the bus 46.

The system 30 includes executable and non-executable (operational) data structures which are stored in a computer readable medium. The computer readable medium may be selected from on or more memory devices 34, including the non-volatile memory 36, ROM 38, or RAM 40. The computer-readable medium may also be a peripheral floppy disk or compact disk accessed through the processor 32.

Other forms of computer-readable media known by those of skill in the art may also be used and are included within the scope of the invention. One skilled in the art will appreciate that portions of the data structures may be stored in various computer-readable media such as the non-volatile memory device 36, ROM 38, RAM 40, floppy disk, compact disk, tape, or the like.

In one presently preferred embodiment, the data structures are stored in the memory device 34 of the system 30. The data structures may be termed as modules and include a model module 50. The model module 50 is executable by the processor 32 and performs the methods discussed above of deriving an accurate model of light scatter. As previously stated, such models are well known in the art. The inodel module 50 may further containing operational particle data relating to the spherical particle to enable an accurate model of light scatter.

The data structures further include a ratio module 52 which is executable by the processor to process the background scatter and particle scatter measurements as discussed above. The ratio module 52 determines the difference in the P and S components of the background light scatter and the particle light scatter to produce the net P and S components. The ratio module 52 further derives the P and S components of the differential scatter cross section. The ratio module 52 also determines the ratios (R and Rps) of the net P and S components of the differential scatter cross section, and the related sizing parameters.

The data structures further include a comparison module 54, executable by the processor 32, to compare Rps to a model ratio. The model ratio is determined by the model module 50. Based on the comparison of Rps to the model ratio, the comparison module 54 determines the particle diameter. Methods for performing this determination are as discussed above.

The present invention performs methods for accurately measuring spherical particle diameters. By performing background measurements and particle measurements an R and Rps ratio may be derived. An analysis and comparison of either the R or Rps ratio with a given model allows for a highly accurate determination of particle measurement. The particles may then be used as standards for calibrating particle scanners.

The invention may be embodied in other specific forms without departing from its spirit or essential characteristics. The described embodiments are to be considered in all respects only as illustrative and not restrictive. Any explanations provided herein of the scientific principles employed in the present invention are illustrative only. The scope of the invention is, therefore, indicated in the appended claims rather than by the foregoing description. All changes within the meaning and range of the claims are to be embraced within their scope.

What is claimed is:

1. A method for accurately measuring the diameter of a surface bound particle comprising the steps of:

directing a beam from a source at an incident angle to a surface;

measuring the light scatter off the surface to determine background scattered light;

measuring the light scatter off the surface bound particle resting on the surface to determine particle scattered light;

determining a net differential scatter cross section from the difference in the background scattered light and the particle scattered light;

determining a sizing parameter from a ratio of the net differential scatter cross section; and comparing the sizing parameter to model parameter values produced by a scatter model for a plurality of particle diameters.

2. The method of claim 1 wherein the sizing parameter is the ratio of the net differential scatter cross section, wherein the net differential scatter cross section is taken at a plurality of scatter angles, and wherein the source is a P polarized source.

3. The method of claim 1 wherein the sizing parameter is the ratio of the net differential scatter cross section, wherein the net differential scatter cross section is taken at a plurality of scatter angles, and wherein the source is a S polarized source.

4. The method of claim 1 wherein the sizing parameter is the ratio of the net differential scatter cross section, wherein the net differential scatter cross section is taken at a plurality of scatter angles, and wherein the source is an arbitrarily polarized source.

5. The method of claim 1 wherein the sizing parameter is the ratio value of the net differential scatter cross section, wherein the net differential scatter cross section is taken at a plurality of scatter angles, wherein the source is an arbitrarily polarized source, and wherein the light scatter is filtered to a polarization other than the arbitrarily polarized source.

6. The method of claim 1 wherein the sizing parameter is determined from a ratioed function of the net differential scatter cross section resulting from the source having different polarizations.

7. The method of claim 6 wherein the sizing parameter is a dip angle associated with the ratioed function.

8. The method of claim 6 wherein the sizing parameter is a minimum dip value associated with the ratioed function.

9. The method of claim 6 wherein the sizing parameter is a dip width value associated with a level greater than a minimum dip value by a chosen amount.

10. The method of claim 6 wherein the sizing parameter is a dip width value associated with the ratioed function, and wherein the ratioed function has a unitary value.

11. The method of claim 6 wherein the sizing parameter is a dip width value associated with the ratioed function, and wherein the ratioed function is an arbitrary constant.

12. A method for accurately measuring the diameter of a surface bound particle comprising the steps of:

directing a beam from a source at an incident angle to a surface;

measuring the light scatter off the surface to determine background scattered light;

measuring the light scatter off the surface bound particle resting on the surface to determine particle scattered light;

determining a net differential scatter cross section from the difference in the background scattered light and the particle scattered light;

determining a ratioed function from the net differential scatter cross section and fitting the ratioed function to model measurements obtained from a scatter model.

13. A computer-usable medium having a computer readable program code embodied therein which causes a computer system to determine the diameter of a surface bound particle resting on a surface by performing the steps of:

receiving background scattered light measurements and particle scattered light measurements resulting from a beam directed from a source at an incident angle at the surface and at the surface bound particle resting on the surface;

determining a net differential scatter cross section from the difference in the background scattered light and the particle scattered light;

determining a sizing parameter from a ratio of the net differential scatter cross section; and comparing the sizing parameter to model parameter values produced by a scatter model for a plurality of particle diameters.

14. The computer-usable medium of claim 13 wherein the sizing parameter is the ratio of the net differential scatter cross section, wherein the net differential scatter cross section is taken at a plurality of scatter angles, and wherein the source is a P polarized source.

15. The computer-usable medium of claim 13 wherein the sizing parameter is the ratio of the net differential scatter cross section, wherein the net differential scatter cross section is taken at a plurality of scatter angles, and wherein the source is a S polarized source.

16. The computer-usable medium of claim 13 wherein the sizing parameter is the ratio of the net differential scatter cross section, wherein the net differential scatter cross section is taken at a plurality of scatter angles, and wherein the source is an arbitrarily polarized source.

17. The computer-usable medium of claim 13 wherein the sizing parameter is the ratio of the net differential scatter cross section, wherein the net differential scatter cross section is taken at a plurality of scatter angles, wherein the source is an arbitrarily polarized source, and wherein the light scatter is filtered to a polarization other than the arbitrarily polarized source.

18. The computer-usable medium of claim 13 wherein the sizing parameter is a ratioed function of the net differential scatter cross section resulting from the source having different polarizations.

19. The computer-usable medium of claim 18 wherein the sizing parameter is a dip angle associated with the ratioed function.

20. The computer-usable medium of claim 18 wherein the sizing parameter is a minimum dip value associated with the ratioed function.

21. The computer-usable medium of claim 18 wherein the sizing parameter is a dip width value associated with a level greater than a minimum dip value by a chosen amount.

22. The computer-usable medium of claim 18 wherein the sizing parameter is a dip width value associated with the ratioed function, and wherein the ratioed function is a unitary value.

23. The computer-usable medium of claim 18 wherein the sizing parameter is a dip width value associated with the ratioed value, and wherein the ratioed function is a constant.

24. An apparatus for measuring the diameter of a surface bound particle resting on a surface comprising:

a processor programmed to execute modules for processing background light scatter measurements and particle light scatter measurements resulting from a beam directed from a source at the surface;

a memory device operably connected to the processor for storing executable and operational data structures, the data structures comprising:

a scatter model module, executable by the processor, containing particle data and effective to determine a model of light scatter from the particle;

a sizing parameter module, executable by the processor, effective to determine a net differential scatter cross section from the background light scatter measurements and the particle light scatter measurements, wherein the sizing parameter module is effective to determine a ratio based on the net differential scatter cross section, wherein the sizing parameter module is effective to determine a sizing parameter based on the ratio; and a comparison module, executable by the processor, effective to compare the sizing parameter to model parameter values produced by the model scatter module for a plurality of particle diameters.

25. The apparatus of claim 24 wherein the sizing parameter is the ratio of the net differential scatter cross section, wherein the net differential scatter cross section is taken at a plurality of scatter angles, and wherein the source is a P polarized source.

26. The apparatus of claim 24 wherein the sizing parameter is the ratio of the net differential scatter cross section, wherein the net differential scatter cross section is taken at a plurality of scatter angles, and wherein the source is a S polarized source.

27. The apparatus of claim 24 wherein the sizing parameter is the ratio of the net differential scatter cross section, wherein the net differential scatter cross section is taken at a plurality of scatter angles, and wherein the source is an arbitrarily polarized source.

28. The apparatus of claim 24 wherein the sizing parameter is the ratio of the net differential scatter cross section, wherein the net differential scatter cross section is taken at a plurality of scatter angles, wherein the source is an arbitrarily polarized source, and wherein the light scatter is filtered to a polarization other than the arbitrarily polarized source.

29. The apparatus of claim 24 wherein the sizing parameter is a ratioed function of the net differential scatter cross section resulting from a source different polarizations.

30. The apparatus of claim 24 wherein the sizing parameter is a dip angle associated with the ratioed function.

31. The apparatus of claim 24 wherein the sizing parameter is a minimum dip value associated with the ratioed function.

32. The apparatus of claim 24 wherein the sizing parameter is a dip width value associated with a level greater than a minimum dip value by a chosen amount.

33. The apparatus of claim 24 wherein the sizing parameter is a dip width value associated with the ratioed function, and wherein the ratioed function is a unitary value.

34. The apparatus of claim 24 wherein the sizing parameter is a dip width value associated with the ratioed function, and wherein the ratioed function is a constant.

* * * * *